(12) United States Patent
Brem et al.

(10) Patent No.: US 6,600,087 B1
(45) Date of Patent: Jul. 29, 2003

(54) EFFICIENT NUCLEAR TRANSFER USING FETAL FIBROBLASTS AND MULTIPLE CLONING PROCEDURES

(75) Inventors: Gottfried Brem, Thalmamsdorf (DE); Gabriela Durcova-Hills, Cambridge (GB); Sigrid Müller, Dadan (DE); Wolfgang Schernthaner, Oberschleissheim (DE); Hendrik Wenigerkind, Diessen (DE); Eckard Wolf, Oberschleissheim (DE); Valeri Zakhartchenko, Oberschleissheim (DE)

(73) Assignee: Agrobiogen GmbH, Hilgerschausen (DE)

( * ) Notice: Subject to any disclaimer, the term of this patent is extended or adjusted under 35 U.S.C. 154(b) by 0 days.

(21) Appl. No.: 09/230,625

(22) PCT Filed: Jan. 16, 1998

(86) PCT No.: PCT/EP98/00230
§ 371 (c)(1),
(2), (4) Date: Jan. 25, 1999

(87) PCT Pub. No.: WO99/36510
PCT Pub. Date: Jul. 22, 1999

(51) Int. Cl.$^7$ .................. C12N 15/00; A01K 67/00; A01K 67/027
(52) U.S. Cl. ................. 800/24; 800/8; 800/15
(58) Field of Search ............... 800/24, 8, 13, 800/15

(56) References Cited

U.S. PATENT DOCUMENTS 5,945,577 A * 8/1999 Stice et al. ............... 800/24
6,011,197 A * 1/2000 Strelchenko et al. ........ 800/24
6,147,276 A * 11/2000 Campbell et al. .......... 800/24

FOREIGN PATENT DOCUMENTS

| WO | WO 97/07669 | 3/1997 |
| WO | WO 98/30683 | 7/1998 |
| WO | WO 98/37183 | 8/1998 |

OTHER PUBLICATIONS

Fehilly et al., Interspecific chimaerism between sheep and goat, Nature, vol. 307, Feb. 16, 1984, pp 634–636.*
Ectors et al., Viability of Cloned Bovine Embryos after one or two clycles of Nuclear Transfer and In Vitro Culture, Theriogenology 44: 925–933, 1995.*
G.A. Presicce et al., Molecular Reproduction and Development, "Nuclear Dynamics of Parthenogenesis of Bovine Oocytes Matured in vitro for 20 and 40 hours and Activated with combined Ethanol and Cycloheximide Treatment," 1994,37:61–68.*
Denman et al (1991) Bio/Technology 9, 839–843.*
Nishimori et al (1984) Gene 29, 41–49.*
Le Huerou et al (1990) Eur. J. Biochem. 193, 767–773.*
Summers et al (1995) Biol. Reproduc. 53, 431–437.*
Campbell, K.H.S. et al., "Nuclear–Cytoplasmic Interactions during the First Cell Cycle of Nuclear Transfer Reconstructed Bovine Embryos: Implications for Deoxyribonucleic Acid Replication and Development," *Biology of Reproduction, 49(5)*:933–942 (Nov., 1993).
Chesne, P. et al., "Nuclear Transfer in Cattle: Birth of Cloned Calves and Estimation of Blastomere Totipotency in Morulae Used as a Source of Nuclei," *Life Science, 316*:487–491 (1993).
Cibelli, J.B. et al., "Cloned Transgenic Calves Produced from Nonquiescent Fetal Fibroblasts," *Science, 280(5367)*:1256–1258 (May, 1998).
Gadbois, D.M. et al., "Multiple Kinase Arrest Points in the $G_1$ Phase of Nontransformed Mammalian Cells are Absent in Transformed Cells," *Proceedings of the National Academy of Sciences (USA), 89*:8626–8630 (Sep., 1992).
Heyman, Y. et al., "Cloning of Domestic Species," *Animal Reproduction Science, 42(1/04)*:427–436 (1996).
Otaegui, P.J. et al., "Transfer of Nuclei from 8–Cell Stage Mouse Embryos following Use of Nocodazole to Control the Cell Cycle," Molecular Reproduction and Development, 39(2):147–152 (Oct., 1994).
Schnieke, A.E. et al., "Human Factor IX Transgenic Sheep Produced by Transfer of Nuclei from Transfected Fetal Fibroblasts," *Science, 278(5346)*:2130–2133 (Dec., 1997).
Wilmut, I. et al., "Viable Offspring Derived from Fetal and Adult Mammalian Cells," *Nature, 385(6619)*:810–813 (Feb., 1997).

* cited by examiner

Primary Examiner—Deborah Crouch
(74) Attorney, Agent, or Firm—Katten Muchin Zavis Rosenman

(57) ABSTRACT

This invention relates to a process for breeding animals through cloning as well as animals obtainable with the process, in particular to a process for the reproduction of animal embryos via an efficient nucleus transfer with foetal fibroblasts.

31 Claims, No Drawings

EFFICIENT NUCLEAR TRANSFER USING FETAL FIBROBLASTS AND MULTIPLE CLONING PROCEDURES

The present invention relates to a process for breeding animals through cloning as well as the animals that can be obtained with the process. This relation relates in particular to a process for cloning animals by an efficient nucleus transfer with specific foetal cells.

Animals, in particular working animals, have been bred by humans for a long time for many different purposes, and developed with regard to particular characteristics. Thus, for example, cows and bulls with a high breeding value for milk yield, were mated in order to obtain animals with a high milking capacity.

In recent years, animals, in particular representatives of the ungulates, such as sheep, cattle and cows have also become the focal point of research interest as production centres of material that are important in terms of nutrition physiology and pharmaceutics, as with the development of genetic engineering it became possible to manufacture in a targeted fashion animals to which a new property, for example, the ability to produce a specific drug, could be given. The problem with the commercial exploitation of such animals, however, is that the genetic construct transferred to them is passed on to their descendants in an integrated and stable manner.

To this end, attempts were made to solve the problem of gene transfer by carrying it out in cells, animals then again being generated from these cells by means of cloning.

Among experts, the term "cloning" is defined generally as the multiplication of a genetic material derived from one single cell, which, transferred to embryology, can be understood as the creation of embryos or animals with an identical genotype. In embryology, the fertilized egg is described as an embryo during blastogenesis, that is, up to the development of the primordium of primitive organs, and as a foetus in the subsequent development stages. Embryonic phases last for different periods of time in different species, thus for example in cattle for a period of about 4 weeks, while shorter or longer periods of time may be required for this for other species within the ungulates.

Up to now, several routes have been followed for cloning animals, that is, for the multiplication of a genotype specific to a particular animal.

On the one hand, early embryonic stages and developments were subjected to microsurgery and the parts isolated from each were bred in vitro or in vivo respectively.

Furthermore, a micromanipulatory combination of asynchronous development stages called "chimeric cloning was carried out in which blastomers from embryos of more advanced stages were brought together with blastomers from earlier stages with the aim of supporting the former in their further development capacity and thus produce identical multiple twins. The largest number of clones obtained in this way, however, was only of the order of 5–8 maximum.

Another procedure was the parthenogenetic activation or mating of homozygous parent animals to obtain clones with regard to specific properties.

However, as the processes named above proved to be relatively poor in terms of effectiveness and reliability, a further process was developed which is generally described as nucleus transfer.

In this process, cell nuclei, which come from multicellular embryos are transferred into suitably prepared egg cells, genetically identical embryos being able to be created.

To be able to carry out a cloning successfully by means of nucleus transfer, however, some in dispensable parameters must be taken into account.

The egg cell that is used as a receptor cell must have completed the metaphase stage in the second division of maturation (metaphase II) and is to no longer contain nucleus DNA of its own, i.e., it is to be present as a so-called enucleated egg cell. Furthermore, the egg cell cytoplasma should be influenced as little as possible, as the substances contained in the cytoplasma itself can be significant for development, for example, the division of the cell.

In addition, the nucleus DNA of the transferred nucleus must be reprogrammed. As the (donor) nucleus comes from a multicellular embryo, the respective donor cell has already passed through some division cycles. This means that the cell is in a development stage which is advanced compared with a totipotent fertilized egg cell in which certain genes which are required for early development are possibly already switched off.

For this reason, the nucleus DNA used must be reprogrammed in such a way that the complete genetic information of the nucleus DNA is available again and the division programme of the embryo begins again at the zygote stage. The better this reprogramming or activation can thus be achieved, the greater the possibility of a successful cloning with which a ready developed cloned animal, i.e. one born alive can then also be obtained.

In addition to the nucleus DNA, the mRNA also present in the cytoplasma is also significant, inter alia, as at the time of the unification of egg cell and donor cell, this represents the messages required for the current development or differentiation stages of the donor cell and the proteins manufactured in this way can have an influence on the further development of the cell.

The process of nucleus transfer has already been used with modest success. Thus, Willadsen et al. reported (Nature 320 (1986), 63–65) on the cloning of lambs, the nuclei coming from nucleus donor cells from the 8-cell stage. Robl et al. (J. Anim. Sci. 64 (1987), 642–647) reported on the first nucleus transfer experiments in cattle, cattle embryos obtained ex vivo being exclusively used as nucleus donors. In these tests, an in vivo intermediate culture in sheep fallopian tubes was always required. In the following years, it was also shown that embryo cloning in cattle can be carried out successfully purely in vitro, i.e. using embryos produced in vitro and egg cells matured in vitro (Sims et al., Proc. Natl. Acad. Sci. USA 91 (1991), 6143–6147).

In WO 97/07668, a process is furthermore described for the reproduction of a an animal embryo in which generally a nucleus with a diploid chromosomal set is transferred to an enucleated egg cell which is maintained in the metaphase stage II, the egg cell first being activated when the nucleus is introduced only after a specific time. By activating the egg cell later after the introduction of the nucleus DNA, an improved reprogramming of the introduced nucleus DNA used is to be achieved.

WO 97/0669 also relates to a process for the reproduction of an animal embryo in which the nucleus of a "quiescent" (dormant) donor cell is transferred into a suitable receptor cell. According to this publication, it is regarded as necessary that the donor cell is fixed in the G0 phase before unification with the receptor cell, which can be achieved by starving the cells or by contact inhibition.

One problem with this technology, however, is still to find suitable donor cells for nucleus transfer with which an animal embryo can most expediently and economically be produced. As is known, reprogramming the nucleus DNA from the respective donor cell chosen presents the greatest difficulty when cloning embryos as this not only influences the further early maturation of the embryos, but also the later development after an implantation into a mother animal that is possibly carried out. Thus, despite all the successes in this area, there are still problems with regard to an effective reprogramming of the donor-nucleus-DNA in order to bring the manipulated egg cell with the new nucleus close to the state of a natural zygote. This is manifested, inter alia, in an extremely small yield with regard to the production of embryonic blastocysts and a low division rate.

One object of the present invention is therefore to overcome the disadvantages of the state of the art and to provide a suitable nucleus-donor cell with which an improved process for cloning animals can be provided.

This object is achieved by a process for cloning an animal embryo in which foetal fibroblasts are used as a donor cell for the nucleus transfer. The nucleus of this cell is combined with a suitable receptor cell and the cell obtained in this Way is grown for a period of time so that a morula forms. The morula that can be obtained in this way can optionally be reused for cloning and be introduced into a mother animal for delivery.

According to a preferred version of the present invention, the receptor cell is an enucleated egg cell into which the nucleus of the foetal fibroblast can be introduced for the nucleus transfer, or with which the foetal fibroblast itself can be fused. The foetal fibroblast can thus be used from a foetus and directly or after a longer period.

The animals in which the process according to the invention can be carried out are, for example, ungulates, rabbits, rodents or birds, with ungulates, in particular pigs, sheep, goats, cattle or cows being preferred.

In a preferred version, the foetal fibroblasts used in the process are transgenic, i.e. they contain one or more genes which are either derived from an exogenous source or which display an endogenous gene introduced to another, non-natural, locus in the genome. These genes preferably code for a drug, for example an antibody or a substance of interest in terms of nutrition physiology, for example chymosin or trypsin, the genes n each case being able to lie under the control of an or the endogenous or an exogenous promoter.

To obtain foetal flbroblasts foetuses are obtained from gravid animals for example, through simple crushing of the foetus. The cells obtained from foetus are then selected on the desired foetal fibroblasts, such as, for example, by adhesion to the culture flask and separation off of the supernatant liquid, or by mechanical selection using a pipette. Because of their phenotype, foetal fibroblasts can be easily distinguished from other cells.

For the subsequent steps, the foetal fibroblast obtained can be used as such, or the nucleus can be isolated from it and used.

As a rule, enucleated egg cells that are matured in vivo or in vitro are used as receptor cells. Thus, for example, unfertilized egg cells matured in vitro can be used in which the surrounding cumulus cells can be removed after reaching metaphase II.

The receptor cell is preferably not to have its own nucleus DNA of its own. To remove the egg cell DNA, there are several possibilities in the state of the art, such as, for example, the division of the egg cell in two halves of which one half no longer has a nucleus and can be used again, or irradiation with ultra-violet light to destroy the DNA peculiar to the cell. It is also possible to remove the nucleus or the pro-nuclei or the metaphase smear by means of micromanipulation. A treatment of the egg cells before the micromanipulation with cytochalasin B with subsequent removal by suction of the zytoplasma lying near the polar body using a pipette, for example carried out with a Leitz microman- ipulator (Leica, Bensheim, Germany) has proved to be preferable. As the nucleus DNA of the egg cell is localised at this point in the vicinity of the polar bodies, the enucleation rate with this method is very high, only a small part of the cytoplasma being removed by suction at the same time.

After the cells involved in the respective nucleus transfer have been obtained, in general two methods can be used. The nucleus of the foetal fibroblast is isolated using processes known and established in the state of the art, and introduced to the prepared receptor cell, such as for example by injection, or the foetal fibroblast itself is fused with the receptor cell.

In a fusion, a foetal fibroblast can be inserted under the zona pellucica of the enucleated egg cell and deposited there using a suitable device such as a transfer pipette. To integrate the cell nucleus of the foetal fibroblast into the cell plasma of the egg cell, the membrane of the fibroblast is fused with the membrane of the egg cell.

Techniques for the fusion of cells are well known in the state of the art, for example, fusion using the sendai virus, treatment with PEG (polyethylene glycol), laser fusion or electroshock. The last-named method, so-called electrofusion, in which pores which make possible a flowing-toguether of the zytoplasma are induced by brief direct-current pulses possibly repeated, for example, 2 to 10 times, of approx. 1 to 5 kV/cm, preferably 1 to 3 kV/cm, with a respective duration of 2 $\mu$secs to 1 sec is preferred in the present process, as the electric pulses can simultaneously bring with them an activation of the (fused) egg cell if they are strong enough. The activation can also take place some hours (approx. 2–5 hours) after the fusion, for example, by incubating the fused cell in a 7 per cent alcohol solution, preferably a 7 per cent ethanol solution, or using other processes known in the state of the art.

The activation of the fused cell is an important step as it is the prerequisite for the start of the division activity of the fusion product. After fusion and activation have taken place, the fibroblast egg cell complexes (nucleus transfer embryos) are bred until they reach a stage in which they can be transferred to a receptor, if required. Substances which support or inhibit the aggregation of microtubules can be added according to choice to the culture medium used. Nocadozol as well as Colcemid are examples for aggregation-inhibiting agents, taxol is a microtubules stabilizer. These substances prevent any formation of several pro-nuclei.

In the existing processes of the state of the art, forming embryos had to be transferred carefully to an intermediate receptor in order to continue breeding them. This was generally achieved by transferring the embryo packed in a protective medium such as agar into the fallopian tubes of a "temporary mother animal" (temporary receptor) in which a further development was necessary until implantation in the (final) mother animal. In the process according to the invention, however, it is also possible to use existing in-vitro systems for cultivation without making the yields worse. Without being bound to a theory, this fact could go with the selection of the donor cell with which embryos can be obtained that very closely resemble naturally created embryos in terms of their development. The cells are cultivated for a certain period, until blastocysts form. This covers a period of up to 10 days, preferably 6 to 7 days.

According to the invention, it is now possible to allow cloned embryos to grow into foetuses that can then in turn be drawn upon as nucleus donors. Within the framework of this so-called recloning, the number of cloned embryos can be further increased.

The foetal fibroblasts for use in the process according to the invention can be obtained from a multitude of animals such as for example mammals, ungulates, rabbits, rodents such as for example rats or mice, or birds such as for example ducks, geese or chickens, for example. Ungulates such as for example cattle sheep, goats, buffalo, camels as well as pigs are preferred for reasons of profitability (economics) among others. Most preferred are sheep or cows.

To facilitate the isolation of the gene product, the gene, product can be directed into a product of the animal itself, in the case of cows or sheep into the milk, for example, or in the case of birds into the eggs. This can be achieved by selecting suitable promoters for organ-specific expression that are known in the state of the art. The gene product can however, equally be obtained from the animal itself, from the serum, for example. It is also possible that the organ(s)/tissue(s) of the animal represent the desired product, for example, for a (xeno-) transplantation.

The foetal fibroblasts or the foetuses used in the process according to the invention or the foetuses or animals from which they are derived can, moreover, be transgenous, the transgene preferably coding for a product which is of interest in terms of nutrition physiology or pharmaceutics, for example an antibody. For example, in cows or sheep, the genes for chymosin or trypsin can be integrated into a construct which makes possible the production of the corresponding enzyme, or of one of its precursors in the animal's milk. The transgene that is of interest can, if desired, be controlled by an exogenous, similarly transgenous promoter, or a known endogenous promoter can be used for this purpose.

With the process according to the invention, it is now possible to achieve an improvement in the production of homologous animal proteins, a modification of in animal products such as milk itself, or the production of animal organs for medical use, for example.

Up to now, a whole series of proteins has been obtained from animal organs by cleaning up from these organs, and then been used in medicine or engineering. Problems occur inter alia concerning the relative quantities in which they are present in these tissues (FSH from pituitary glands, for example), which leads to high production costs, as a large quantity of source material, i.e. many animals, are needed, which, due to the multitude of animals involved, brings with it the danger of contamination with for example pathogens such as BSE or Ehec.

Examples of interesting proteins from animal organs are aprotinin from the lung, chymosin from the stomach, catalase from the liver, elastase, pancreatin, instilin or trypsin from the pancreas, hyaluronidase from testicles, chondroitin from the trachea, collagen from the skin, fibronectin or vitronectin from plasma, epithelial cell growth suppl. or LH (luteinizing hormone) from the pituitary gland, fibroblast growth factor or ganglioside from the brain as well as haemoglobin, thrombin, transferrin and so on. This list is not to be seen as exhaustive.

For all these products, an ectopic expression, i.e. an expression in another tissue, for example, in the lacteal gland can be achieved, if an additive gene transfer has previously been carried out in the cells used for cloning, for example by injection, transformation, transfection, or another process known in the state of the art was used, an in vitro recombined gene construct additionally being integrated into the genome. In addition to this, homologous recombination in the cells enables the endogenously present gene to be combined with a promoter which produces a different expression pattern for this structure gene, for example, production of chymosin in the udder with accompanying secerning into the milk instead of the endogenous synthesis in the stomach. Furthermore, an endogenously present promoter, for example, the casein or lactoglobulin promoter, can be coupled with a new structure gene so that conditions for the expression are optimal. In both the cases described above, promoter and structure gene that are recombined homologously into the genome, can be isolated beforehand from a gene bank that was obtained for example from foetal fibroblasts so that not is species-specific DNA (self-cloning) used, but also the DNA is isogneous.

In this way, the composition of foodstuffs obtained from animal products such as for example milk can therefore be modified as desired so that they have positive alimentary, dietary, health-promoting properties or a reduced allergen potential, improved storage stability or processing properties. Thus, for example, milk can be manufactured with Ehec antibodies or with properties specially designed to combat illnesses such as for example lactose intolerance.

Moreover, by using MACs (mammalian artificial chromosomes), integration mutations are avoided and large DNA fragments transferred. These MACs are replicated as additional mini- or microchromosomes in the nucleus in exactly the same way as the endogenous chromosomes. In this way, it is possible, for example, to transfer gene clusters beyond the species, for example, to transfer complete human immunoglobulin gene clusters to working animals, the working animal then having the ability to produce human antibodies that could be obtained and used. The transfer of specific MACs from one's own species also means that additive gene effects would lead to an increase in the synthesis of the gene product.

Also important is an expression of homologous proteins, or tissues or organs in working animals, for proteins in the same organs in which these proteins are also expressed in humans. The proteins are then obtained using processes known in the state of the art, and the tissues or organs removed from the animal before any transplantation. The advantage of this procedure is a high identity of the expressed proteins, as they are processed or post-translationally modified in the correct organ, for example, expression of erythropoietin in the kidney. This means that the proteins obtained from the different tissues have the same glycosylation as the substances in humans themselves, their activity closing resembling that of the natural protein. In this way, transgenic animals for example pigs, cattle, etc., for example, can be obtained that produce human insulin, erythropoietin etc. which can then be used better in medicine.

Using the process according to the invention, once a working animal has been made transgenic it can be propagated in a stable manner with for example the properties listed above.

The present invention also covers the cloned animals that can be obtained with the process according to the invention which, as explained above, can be transgenous or not.

One advantage of the process according to the invention is that, in addition to avoiding the need to bring the cells into the G0 phase, the efficiency with regard to yields when recloning is constant and even increased.

Thus, when using the process according to the invention, results were achieved that were even better than those resulting from punctured oocytes with subsequent maturation and fertilisation—without cloning, however. The higher in vivo development capacity observed increases the efficiency of the cloning programmes significantly.

The so-called gravidity rate (pregnancy rate), which can be determined as the proportion of animals that have become pregnant after the transfer of embryos cultivated in vitro for 6—7 days to synchronized receptor animals, serves as a measure of the efficiency of such processes. The respective gravidity rates can be determined by measuring the progesterone level. ultrasound examinations, or by means of rectal palpation.

Taking cattle as an example, the following results were obtained using different processes:

| Gravidity rates: | |
| --- | --- |
| Oocyte puncture with subsequent IVM and IVF | 34% |
| Embryo cloning (average) | 25% |
| Embryo cloning with foetal fibroblasts | 55% |

IVM = in vitro maturation
IVF = in vitro fertilisation

The invention will now be explained in more detail by reference to the example, which is given merely for explanatory purposes and is not intended to restrict the scope of the invention.

EXAMPLE

Isolation of Foetal Fibroblasts in Cattle Foetus

Foetuses from uteruses of slaughtered calves or cows were prepared outside and brought into the laboratory in PBS (phosphate-buffered saline, without $CA^{2+}/Mg^{2+}$, with penicillin/streptomycin, plus 10% of foetal calf serum (FCS) on ice. The foetuses were then washed several times with fresh PBS. After washing, the head and internal organs were removed from the foetuses, and the latter washed in PBS again, crushed in 5 ml PBS and transferred into a 50 ml culture tube. After the addition of 10 ml PBS, centrifuging was carried out carefully for 5 mins at 300 rpm, and the pellet was resuspended in 0.1 per cent trypsin solution. After a 5-minute incubation at 37° C., it was transferred into a 50 ml centrifugal tube in which centrifuging was carried out again (300 Rpm/5 mins). These steps, beginning with the trypsin treatment, were repeated twice. The cell suspension thus obtained was then filtered, transferred into a 50 ml tube, centrifuged for 5 mins (160g), the pellet resuspended and absorbed in 1 ml culture medium (Dulbecco's modified Eagle Medium (Gibco), supplemented by 15% FCS, 2mM L-glutamine, $10^{-7}$ mMol β-mercaptoethanol, and penicillin/streptomycin).

After the trypsin treatment, the cell suspension was placed in 10 cm culture dishes and bred in a culture medium (supra) with 10% FCS (Biochrom. Berlin) (37° C. 5% $CO_2$) until the cell growth was subconfluent (2 to 3 days). One part of this passage "0" was frozen (10% dimethyl sulphoxide, Sigma) and stored in liquid nitrogen.

As a comparison of the process, one part of the fibroblasts was synchronised before nucleus transfer into a presumptive G0-phase according to the procedure described in the WO 97/07669 (Campell et al.) by strong reduction of the serum concentration in the culture. One day after the passage, cells were then washed three times with PBS and then bred in fresh medium with 0.5% FCS for 8 days (starvation, "starved cells") before being used for cloning. In the process described by Campell, transferring the fibroblasts used into the G0-phase by "starvation" or other processes is seen as unavoidable.

The fibroblasts for the process described here which were not exposed to this starvation process, were taken directly from the subconfluent cell culture and used for cloning without further treatment.

Furthermore, blasiomeres (embryonic cells) from morulae (embryos aged approximately 6 days with a cell count of between 30 and 70 blastomeres) that formed from cloning with starved and non-treated fibroblasts were re-used for cloning (recloning). The results are listed in the table and show that despite working against the teaching of the state of the art, even better results can be obtained.

The obtained gravidity rates were also surprisingly found to be 60%.

Additive Gene Transfer

In vitro recombined gene constructs such as described in DE-OS-40 12 526, reference to which is also included here, are integrated into a stable manner in the nuclei of isolated foetal fibroblasts by conventional DNA microinjection (Brem G., Transgenic Animals, Genetic Engineering of Animals, VCH Weinheim (1993), 83–170) or by known transformation procedures (Maniatis et al., Molecular Cloning, A Laboratory Manual, Cold Spring Harbor Laboratory, 1989). The proof of the integration in the cells is provided by means of PCR and/or Southern Blotting (Maniatis, above). An expression in differentiated-out cells shows that the gene transfer has been successful.

Cloning

18–20 hours after the beginning of maturation, bovine oocytes isolated from the egg supply were separated from the cumulus cells surrounding them and enucleated within two hours (Molecular Reproduction and Development 42 (1995). 53–57). About 20–22 hours after the onset of maturation, foetal fibroblasts obtained as above were transferred by means of a transfer pipette into the perivitelline space of enucleated oocytes and the forming karyoplast-cytoplast complexes (KCC) were each exposed to a double electric pulse of 2.1 kV/cm for 10 μsecs in order to induce fusion. The KCCs were bred in Ham's F-12 medium (Sigma) with 10% FCS in a incubator. The fusion was assessed by microscopic examination 30 to 60 minutes after the fusion pulse.

24 hours after the onset of maturation, the KCCs were activated by a 5-minute incubation in 7% ethanol and subsequently bred for 5 hours in 10 μg/ml cycloheximide (Sigma C-7698) and 5 μg/ml cytochalasin B (Sigma C-6762). Subsequently, the KCCs were reacted in a 100 μl-drop CR-1 medium (Rosenkrans and First, 1991) with 10% oestrus-cow serum. The drops were coated with paraffin oil and bred for 7 to 8 days at 39° C. in a steam-saturated atmosphere comprising 5% $Co_2$, 59% $O_2$ and 90% $N_2$.

TABLE 1

| Morulae from foetal fibroblast cloning (FFB) as nucleus donors | | | | |
| --- | --- | --- | --- | --- |
| Nucleus transfer morulae from cloning | KCC | Fused FFB (%) | Division (%) | Blastocysts (%) |
| FFB (not starved) | 65 | 58 (89%) | 50 (86%) | 32 (55%) |
| FFB (starved) | 102 | 91 (88%) | 73 (80%) | 47 (52%) |

As can be seen from the above table, it was already possible during the first experiment to obtain a division rate of up to 86% and a blastocyst rate of up to 55%. This is to be seen as surprising, in view of the fact that it is seen as necessary in the state of the art to "starve" the fibroblasts, as results can be attained that are even better compared with the state of the art.

Embryo Transfer

Receptor Management

The receptors used were calves that fulfilled the following criteria:

1. Raised on farms where IBR (bovine herpes virus type 1) is not suspected;
2. Serological examination for BHV-1-antibodies (infectious bovine rhinotracheitis/infectious pustulous vulvovaginitis) negative;
3. Serological examination for BVD (bovine virus diarrhea)/MD-antigen (mucosal disease) negative;
4. Body weight development corresponding to age (13–16 months);
5. Sexual maturity for animals that are to carry the embryo, breeding maturity;
6. Gynaecological examination without pathological findings;

All receptors received mineral bolusses directly after stabling in order to compensate for what experience shows to be insufficient supply of selenium, copper and cobalt (Wittkowski et al., Zur Selensupplementierung bei Färsen (supplementing selenium in heifers); Annual Conference of the Arbeitsgemeinschaft Embryotransfer Deutschland (AET-d). 13.06.–14.06.1996, Marktredwitz).

BVD antibodies negative animals are immunised against BVD/MD (Rumilis®, Intervet) to minimise the risk of infection when transferring embryos (Mödl et al., Control of bovine viral diarrhea virus in abattoir ovaries for in vitro fertilization (IVF) or cloning programs; 11th meeting A.E.T.E.-Hannover, 8–9 September 1995) or after placement in stables with unknown BVD status. Feeding was carried out ad libitum with grass silage, hay and straw. Worming was carried out in spring and autumn with Ivermectin (Ivomec®, MSD Agvet). The receptors were housed partly in loose housing barn (open yard, group size 6 animals) and partly in tying stalls.

Receptor Preparation

The embryos manufactured in vitro are transferred onto cycle-synchronous receptors, i.e. the stage of the sexual cycle corresponds to the age of the embryos to be transferred. The day of oestrus is designated cycle day 0. Oestral synchronisation is carried out in the dioestrus by the single intermuscular application of a protaglandin $F_2\acute{a}$-analog (2.0ml Estrumate®, Mallinckrodt Veterinary). Calves in which no functional corpus of luteum was diagnosable by means of rectal palpation were not used for oestral synchronisation. Experience shows that oestrus usually appears 2–3 days after application and is assessed by reference to oestral behaviour and vaginal findings.

Embryo Transfer

The embryos produced in vitro were transferred onto suitable receptors after 7-day cultivation. For this, the embryos were identified, qualitatively assessed zone-slit, converted into a suitable transfer medium and subsequently bred in mini paillettes (Minitüb). PBS +10% fetal calf serum (FCS, Biochrom), ovum culture medium (ICP, New Zealand) +10% FCS or TL-Hepes +10% FCS were used as transfer media.

The sealed paillettes were stored at 37.8° C. in a mini incubator until the transfer, which should take place within approx. 90 minutes.

The suitability of the receptors was assessed using the following criteria:

The animals were observed for about 7 days before transfer in oestrus, the asynchronisity not to exceed 24 hours (Hasler et al., Theriogenology 43 (1995), 141–152). The presence and size of a functional yellow body were evaluated accordingly (Assey et al., Theriogenology 39 (1993), 1321–1330).

The animals used did not show any sign of disease of the genital tract.

After the selection, an epidural anaesthesia (2.0ml Lidocain®, Albrecht) was undertaken and the outer genitalia carefully cleaned with dry paper. The transfer catheter at body temperature (Minitüb) was subsequently charged with a paillette and provided with a plastic protective sheath (Sanisheath, Minitüb). The transfer was non-operative with rectal monitoring of the cervix passage and the catheter position into the top of the ipsilateral uterus horn (Reichenbach et al., J. Reprod. Fertil. 95 (1992), 363–370). The plastic protective sheath was first perforated with the transfer catheter at the outer uterine orifice to prevent the spread of germs from the vagina into the uterus. If it was planned to transfer several embryos onto one receptor, these were deposited bilaterally. To do this, the transfer catheter was pulled back as far as the body of the uterus, the mandrin with the empty paillette removed, a new paillette with embryo(s) inserted in the catheter and positioned in the contralateral uterus horn. Directly after the transfer, all relevant data (life number of the receptor, origin, number and quality of the embryos, etc.) was documented.

Pregnancy Examination 21 days after oestrus, i.e. 14 days after embryo transfer, an oestral check was carried out and the progesterone content in the blood serum determined. Values under 0. 1 ng/ml are regarded as not pregnant. In the case of progesterone values of over 2.0 ng/ml, a pregnancy can be counted on. The first direct pregnancy examination was carried out by ultrasound around the 35th day and the second manually around the 42nd day of pregnancy.

What is claimed is:

1. A process for the production of a bovine embryo comprising the following steps:
   (a) obtaining a bovine fetal fibroblast comprising a nucleus;
   (b) combining the nucleus of the fetal fibroblast with a bovine enucleated oocyte, the fetal fibroblast not being fixed by external manipulation in the GO phase before the combination, to produce a first karyoplast-cytoplast complex (KCC);
   (c) activating the first KCC by,
      (i) incubating the first KCC in medium comprising about 7% ethanol for about 5 minutes;
      (ii) incubating the first KCC of Step (c)(i) in a medium containing cycloheximide and an effective amount of microtubule aggregation inhibitor;
   (d) growing the activated KCC of step (c)(ii) in culture medium so that an embryo forms;
   (e) obtaining a cell from the embryo of step (d) comprising a nucleus;
   (f) combining the nucleus of the cell of step (e) with a bovine enucleated oocyte to produce a second KCC;
   (g) activating the second KCC by,
      (i) incubating the second KCC in medium comprising about 7% ethanol for about 5 minutes;
      (ii) incubating the second KCC of Step (g)(i) in a medium containing cycloheximide and an effective amount of microtubule aggregation inhibitor;

(h) growing the activated KCC of step (g)(ii) in culture medium so that blastocyst form; and optionally (i) implanting the blastocyst into a female bovine thereby permitting development of a fetus from the blastocyst.

2. The process according to 1 wherein the fetal fibroblast comprises a transgene and is used to produce a transgenic bovine.

3. The process according to 2 wherein the transgene encodes a gene product that is secretable into the milk of the bovine.

4. The process according to 2 herein the transgene encodes a pharmaceutical or nutritional product.

5. The process according to 4 wherein the transgene encodes a gene product that is secretable into the milk of the bovine.

6. The process according to claim 5 wherein the transgene encodes a precursor of chymosin or trypsin.

7. The process according to claim 1 wherein the fetal fibroblast is fused with the enucleated oocyte.

8. The process according to 7 wherein the fetal fibroblast comprises a transgene and is used to produce a transgenic bovine.

9. The process according to 8 wherein the transgene encodes a gene product that is secretable secreted into the milk of the bovine.

10. The process according to 8 wherein the transgene encodes a pharmaceutical or nutritional product.

11. The process according to 10 wherein the transgene encodes a gene product that is secretable secreted into the milk of the bovine.

12. The process according to claim 11 wherein the transgene encodes a precursor of chymosin or trypsin.

13. The process according to claim 1 wherein the substance that inhibits microtubule aggregation is cytochalasin B.

14. The process according to 13 wherein the fetal fibroblast comprises a transgene and is used to produce a transgenic bovine.

15. The process according to 14 wherein the transgene encodes a gene product that is secretable secreted into the milk of the bovine.

16. The process according to 14 wherein the transgene encodes a pharmaceutical or nutritional product.

17. The process according to 16 wherein the transgene encodes a gene product that is secretable secreted into the milk of the bovine.

18. The process according to claim 17 wherein the transgene encodes a precursor of chymosin or trypsin.

19. The process according to claim 1 wherein the embryo of step (d) is a fetus.

20. The process according to 19 wherein the fetal fibroblast comprises a transgene and is used to produce a transgenic bovine.

21. The process according to 20 wherein the transgene encodes a gene product that is secretable secreted into the milk of the bovine.

22. The process according to 20 wherein the transgene encodes a pharmaceutical or nutritional product.

23. The process according to 22 wherein the transgene encodes a gene product that is secretable secreted into the milk of the bovine.

24. The process according to claim 23 wherein the transgene encodes a precursor of chymosin or trypsin.

25. The process according to claim 1 wherein the embryo of step (d) is a blastocyst.

26. The process according to 25 wherein the fetal fibroblast comprises a transgene and is used to produce a transgenic bovine.

27. The process according to 26 wherein the transgene encodes a gene product that is secretable secreted into the milk of the bovine.

28. The process according to 26 wherein the transgene encodes a pharmaceutical or nutritional product.

29. The process according to 28 wherein the transgene encodes a gene product that is secretable secreted into the milk of the bovine.

30. The process according to claim 29 wherein the transgene encodes a precursor of chymosin or trypsin.

31. The process according to any one of claims 2–6, 8–12, 14–18, 20–24, 26–27, or 30 wherein the transgene is operatively linked to a promoter.

* * * * *